(12) United States Patent
Swaile et al.

(10) Patent No.: US 12,420,120 B2
(45) Date of Patent: Sep. 23, 2025

(54) ANTIPERSPIRANT AND DEODORANT COMPOSITIONS FOR INCREASED SKIN LUBRICITY

(71) Applicant: The Procter & Gamble Company, Cincinnati, OH (US)

(72) Inventors: David Frederick Swaile, Cincinnati, OH (US); Rajeev Kumar Passi, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1066 days.

(21) Appl. No.: 17/209,288

(22) Filed: Mar. 23, 2021

(65) Prior Publication Data

US 2021/0308492 A1 Oct. 7, 2021

Related U.S. Application Data

(60) Provisional application No. 62/993,812, filed on Mar. 24, 2020.

(51) Int. Cl.
| | | |
|---|---|---|
| *A61Q 15/00* | (2006.01) | |
| *A61K 8/891* | (2006.01) | |
| *A61K 8/892* | (2006.01) | |
| *A61Q 9/02* | (2006.01) | |
| *B26B 21/00* | (2006.01) | |
| *B26B 21/40* | (2006.01) | |

(52) U.S. Cl.
CPC .............. *A61Q 15/00* (2013.01); *A61K 8/891* (2013.01); *A61K 8/892* (2013.01); *A61Q 9/02* (2013.01); *B26B 21/00* (2013.01); *B26B 21/4081* (2013.01)

(58) Field of Classification Search
None
See application file for complete search history.

(56) References Cited

U.S. PATENT DOCUMENTS

| 5,650,146 | A | 7/1997 | Shaw | |
|---|---|---|---|---|
| 2004/0120909 | A1 | 6/2004 | Lee et al. | |
| 2011/0056506 | A1 | 3/2011 | Petraia et al. | |
| 2012/0009285 | A1* | 1/2012 | Wei | A61K 8/19 |
| | | | | 514/552 |
| 2013/0045256 | A1 | 2/2013 | Schwartz | |
| 2017/0100325 | A1* | 4/2017 | Swaile | A61Q 15/00 |

FOREIGN PATENT DOCUMENTS

| EP | 1549286 B1 | 7/2012 |
|---|---|---|
| EP | 2797570 B1 | 12/2018 |
| WO | 2010129235 A2 | 11/2010 |

OTHER PUBLICATIONS

PCT Search Report and Written Opinion for PCT /US2021/023838 dated Jul. 5, 2021, 13 pages.

* cited by examiner

*Primary Examiner* — Anna R Falkowitz
*Assistant Examiner* — Garen Gotfredson
(74) *Attorney, Agent, or Firm* — Alexandra S. Anoff; Kathleen Y. Carter

(57) ABSTRACT

A method of removing hair from an underarm comprising the steps of applying an antiperspirant or deodorant composition to the underarm and shaving the underarm with a razor; wherein said antiperspirant or deodorant composition comprises a component selected from the group consisting of an antiperspirant active, a deodorant active, an odor masking fragrance, and combinations thereof; and wherein the composition comprises from about 3% to about 20%, by weight of the composition, of a blend of a nonvolatile, low viscosity silicone emollient and a high molecular weight silicone polymer.

14 Claims, 2 Drawing Sheets

ANTIPERSPIRANT AND DEODORANT COMPOSITIONS FOR INCREASED SKIN LUBRICITY

FIELD OF THE INVENTION

The present invention is directed to antiperspirant and deodorant compositions capable of increasing skin lubricity, particularly when shaving. The antiperspirant and deodorant compositions may take many different product forms including, but not limited to, a solid stick, a roll-on, a soft solid, a gel, and a spray product.

BACKGROUND OF THE INVENTION

Deodorant and antiperspirant products are well known in the art. These products are typically applied to the underarm. These products provide a deodorancy benefit and/or an antiperspirancy benefit, depending on the type and composition of the product. These benefits have been well documented with deodorant and antiperspirant products.

While the benefits of deodorant and antiperspirant products have been well documented, other needs related to skin care, particularly underarm care, have been overlooked. For example, underarm irritation remains a major consumer negative, as the skin of the underarm is particularly sensitive in some individuals. A major cause of underarm irritation involves shaving the underarm skin. Shaving the underarm has historically produced irritation of the underarm. While shave preparations and hair removing implements have been designed to address this problem, there still exists an opportunity to reduce irritation of the underarm, particularly as an additional function of the antiperspirant or deodorant product that many consumers are already wearing daily. This invention addresses those needs.

SUMMARY OF THE INVENTION

A method of removing hair from an underarm comprising the steps of applying an antiperspirant or deodorant composition to the underarm and shaving the underarm with a razor; wherein said antiperspirant or deodorant composition comprises a component selected from the group consisting of an antiperspirant active, a deodorant active, an odor masking fragrance, and combinations thereof; and wherein the composition comprises from about 3% to about 20%, by weight of the composition, of a blend of a nonvolatile, low viscosity silicone emollient and a high molecular weight silicone polymer.

DETAILED DESCRIPTION OF THE INVENTION

Figure 1:
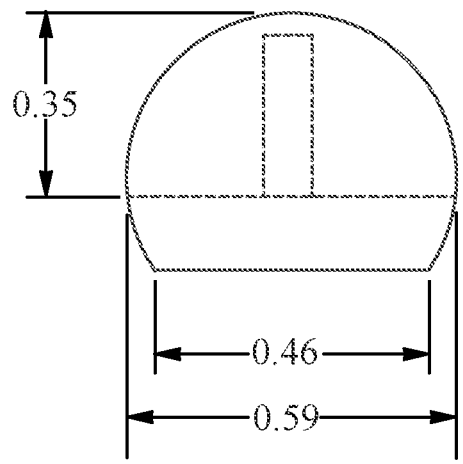
FIGS. 1-4 show the custom-made aluminum probe to be used in the coefficient of friction test method.
Figure 2:
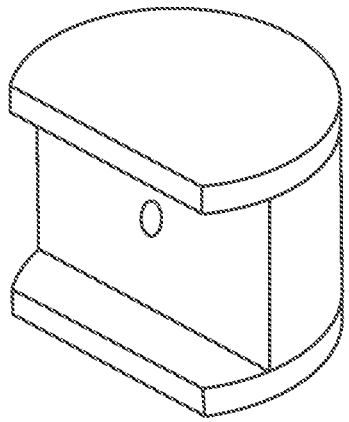
Figure 3:
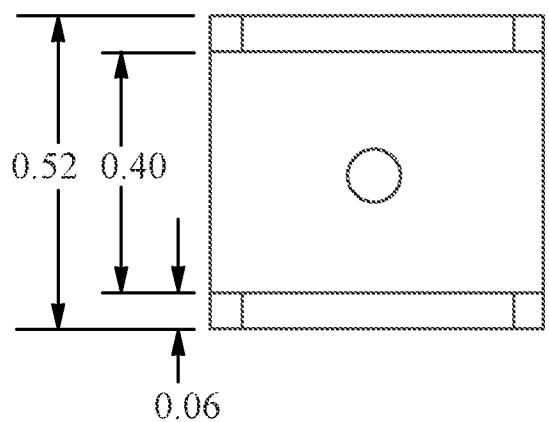
Figure 4:
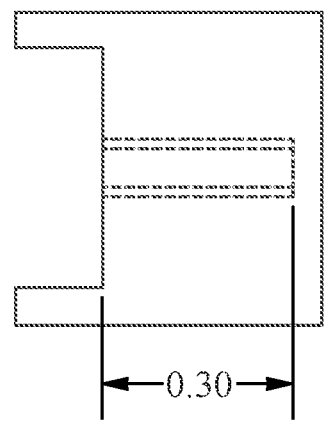

The present invention may be understood more readily by reference to the following detailed description of illustrative and preferred embodiments. It is to be understood that the scope of the claims is not limited to the specific ingredients, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

All percentages and ratios used herein are by weight of the total composition, and all measurements made are at 25° C., unless otherwise designated.

The compositions of the present invention can comprise, consist of, and consist essentially of the elements and limitations of the invention described herein, as well as any of the additional or optional ingredients, components, steps, or limitations described herein.

The term "ambient conditions" as used herein refers to surrounding conditions at about one atmosphere of pressure, about 50% relative humidity and about 25° C.

The term "volatile" as used herein refers to those materials which have a measurable vapor pressure as measured at 25° C. and 1 atmosphere. The term "moderately volatile material," as used herein, refers to those materials with a vapor pressure below about 2 mmHg at 25° C. The term "low volatile material," as used herein, refers to those materials with a vapor pressure below about 0.5 mmHg at 25° C. The term "nonvolatile material," as used herein, refers to those materials with a vapor pressure below about 0.002 mmHg at 25° C. Vapor pressures can be measured in a variety of manners and are often available in a variety of chemical data bases that would be known to one skilled in the art. One such database is available from the Research Institute for Fragrance Materials.

Applicants have unexpectedly discovered that irritation as a result of shaving the underarm area can be reduced by utilizing an antiperspirant or deodorant product or composition having a blend of a nonvolatile, low viscosity silicone emollient and high molecular weight silicone polymer, such as dimethicone and dimethiconol. The underarm composition of the present invention reduces irritation by reducing the friction of the razor against the skin, hereafter referred to as skin friction. Without wishing to be bound by theory, it is believed that the antiperspirant or deodorant composition comprising the blend of the present invention minimizes irritation by having high substantivity on the skin. The blend of a low viscosity silicone emollient and a high molecular weight silicone polymer is able to remain on the skin even after a first stroke of a razor or multiple strokes. Thus, the material can maintain its ability to deliver increased lubricity and reduced skin friction throughout the shaving regimen. Specifically, it is believed that the terminal hydroxy groups of the high molecular weight dimethiconol are capable of hydrogen bonding to the skin, which enhances its skin substantivity while wearing the product and during the shaving process.

Moreover, this invention also does not require a habit change for the group of consumers that do not utilize any shave preparation on their underarm. Applying the product of the present invention as a typical antiperspirant or deodorant product delivers the benefit of the reduced irritation, even after being worn for a period of time.

I. Exemplary Deodorant and Antiperspirant Compositions

Deodorant and antiperspirant compositions of the present invention may include a blend of a nonvolatile, low viscosity silicone emollient and a high molecular weight silicone polymer, such as dimethicone and dimethiconol. Compositions may further include a product chassis and any number of optional ingredients that are described below and/or are known to the skilled artisan. Blends of a nonvolatile, low viscosity silicone emollient and high molecular weight silicone polymer The blend of a nonvolatile, low viscosity silicone emollient and high molecular weight silicone polymer in the present invention may be present from about 3% to about 20% of the composition by weight, alternatively from about 5% to about 20% of the composition, alternatively from about 8% to about 15% of the composition, alternatively from about 10% to about 15% of the composition by weight, where the composition is in a solid, semi-solid, or aerosol form (excluding the propellant). The blend of a nonvolatile, low viscosity silicone emollient and high molecular weight silicone polymer in the present invention may be present from about 10% to about 40% of the oil-phase of the composition, alternatively from about 15% to about 30% of the oil phase of the composition, where the composition is a gel or a roll-on.

The blend of a nonvolatile low viscosity silicone emollient and high molecular weight silicone polymer, such as dimethicone and dimethiconol, may be created prior to or during the product making process. Pre-blending is often preferred to allow the high molecular weight silicone polymer to be fully solvated by the low viscosity silicone emollient. The blend of a nonvolatile low viscosity silicone emollient and high molecular weight silicone polymer, such as dimethicone and dimethiconol, typically will have less than about 30% by weight of high molecular weight silicone polymer. It is preferred to have from about 5% to about 20% high molecular weight silicone polymer in the blend to create a blend with a viscosity that is easily incorporated into the product and more preferred to have from about 10% to about 15% high molecular weight silicone polymer in the blend. The high molecular weight silicone polymer may have a molecular weight greater than about 100 kilodaltons, or in some embodiments greater than about 300 kilodaltons, or in some other embodiments greater than about 500 kilodaltons. The nonvolatile low viscosity silicone emollient may have a viscosity less than about 100 cps and a vapor pressure less than about 0.10 mm of Hg.

Suitable commercial blends of a nonvolatile, low viscosity silicone emollient and a high molecular weight silicone polymer include, but are not limited to, DC1503, DC1413, and CB-1556 from Dow Chemical, Silsoft 8812 and SF1236 from Momentive Silicones, SPI-5403B from Silicone Plus, X-21-5613 from Shinetsu silicones, and Mirasil D-DML HV from Elkem Silicones.

Suitable high molecular weight silicone polymers may include, but are not limited to, X-21-5847 and X-21-5849 from Shinetsu silicones, Mirasil DM 500000 silicone and Mirasil DM 300 000 silicone from Elkem Silicones.

Suitable nonvolatile, low viscosity silicone emollients may include, but are not limited to, linear dimethicone emollients with a viscosity from about 5 cst about 100 cst. Other low viscosity silicone solvents such as phenyl trimethicone may also be employed.

In some embodiments, the nonvolatile, low viscosity silicone emollient may be a blend of multiple nonvolatile, low viscosity silicone emollients. Similarly, in some embodiments, the high molecular weight silicone polymer may be a mixture of multiple high molecular weight silicone polymers.

II. Product Forms

Antiperspirant and deodorant compositions can be formulated in many forms. For example, an antiperspirant or deodorant composition can be, without limitation, a roll-on product, a gel, a stick including soft solid sticks and invisible solids, or an aerosol including both deodorant or antiperspirant sprays. Each of the antiperspirant and deodorant compositions described below can include a substantive friction reducer comprising a blend of a nonvolatile, low viscosity silicone emollient and a high molecular weight silicone polymer, as described herein.

A. Roll-On and Gel

A roll-on or gel antiperspirant or deodorant composition can comprise, for example, water, emollient, emulsifiers, deodorant or antiperspirant actives, or combinations thereof.

Water

The roll-on or gel composition can include water. Water can be present in an amount of about 1% to about 99.5%, about 25% to about 99.5%, about 50% to about 99.5%, about 75% to about 99.5% about 80% to about 99.5%, from about 20% to about 60%, from about 40% to about 70% or any combination of the end points and points encompassed within the ranges, by weight of the deodorant composition.

Emollients

Roll-on or gel compositions can comprise an emollient system including at least one emollient but may also comprise a combination of emollients. Suitable emollients are often liquid under ambient conditions. Depending on the type of product form desired, concentrations of the emollient (s) in the deodorant or antiperspirant compositions can range from about 1% to about 95%, from about 5% to about 95%, from about 15% to about 75%, from about 1% to about 10%, from about 15% to about 45%, or from about 1% to about 30%, by weight of the deodorant or antiperspirant composition.

Emollients suitable for use in the roll-on and gel compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises for roll-ons is PPG-15 stearyl ether. Examples of suitable emollients for a gel are cyclopentasiloxane and dimethicone. Other examples of suitable emollients or both forms include dipropylene glycol and propylene glycol.

Emulsifier

The composition can contain an emulsifier. A suitable emulsifier can be, for example, a polymeric or nonpolymeric surfactants. Suitable surfactants are nonionic surfactants, cationic surfactants, amphoteric surfactants, zwitterionic surfactants, and mixtures thereof. Often roll-ons employ emulsifiers suitable for oil in water emulsions. Examples of emulsifiers for gel compositions include those suitable for water in silicone or water in oil emulsions.

Suitable emulsifiers for roll-on products include, for example, polyoxyethylene 2 stearyl ether, polyoxyethylene 20 stearyl ether, polyoxyethylene 21 stearyl ether, ceteth-10, ceteareth-2, and combinations thereof. Suitable emulsifiers for gel compositions include but are not limited to PEG/PPG-18/18 Dimethicone (DC5225), Lauryl PEG/PPG-18/18 methicone, Dimethicone/PEG-10/15 Crosspolymer, and combinations thereof.

When the emulsifier is present, it is typically present at a level of from about 0.01% to about 10%, alternatively from about 0.01% to about 3%, alternatively from about 0.05% to about 1%, alternatively from about 0.01% to about 0.05%, by weight of the composition.

Deodorant Actives

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise Piroctone olamine, cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, triethylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Antiperspirant Active

The gel compositions can comprise an antiperspirant active suitable for application to human skin. The concentration of antiperspirant active in the composition should be sufficient to provide the desired perspiration wetness and odor control from the antiperspirant roll-on or gel formulation.

The roll-on or gel compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. Often antiperspirant actives used in roll-on or gel compositions are provided as an aqueous solution.

The antiperspirant active for use in the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts.

Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]}$-$AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Some embodiments of the present invention may comprise no antiperspirant active, and some embodiments may comprise only a deodorant active.

B. Stick Products

Stick products including solid, invisible solid, and soft solid antiperspirant and or deodorant compositions as described herein can contain a primary structurant and sometimes additional structurants, emollients, an antiperspirant and/or deodorant active, a perfume, perfume delivery composition, and additional chassis ingredient(s). These antiperspirant and or deodorant composition may be anhydrous. The antiperspirant and or deodorant composition may be free of added water.

Hardness

The compositions can be in the form of a solid stick including invisible solids. The stick compositions can have a product hardness of about 600 gram·force or more. The solid or invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force. Moreover, the compositions can form a soft solid that is often rubbed onto the skin via a package with an application surface. The soft solid stick compositions can have a product hardness of less than about 600 gram·force, specifically from about 100 to 500 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Structurants

The stick formulation can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant and or deodorant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol, cetyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides such as tribehenin and C18-C36 triglyceride; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Emollients

The stick composition can comprise an emollient or mixture of emollients at concentrations ranging from about 20% to about 80%, and more specifically from about 30% to about 70%, by weight of the composition. The emollient can be a volatile silicone which may be cyclic or linear. The emollient can a be a nonvolatile silicone that is linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant compositions include those represented by the formula:

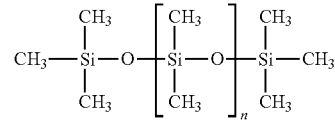

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Nonvolatile Emollient

Nonvolatile emollients may be also present in these compositions. Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate. The nonvolatile emollient could also comprise a silicone emollient such as dimethicone with a viscosity of 5 cst or greater.

Antiperspirant Active

The antiperspirant stick compositions can comprise an antiperspirant active suitable for application to human skin, similar to those described herein. For antiperspirant stick compositions, the antiperspirant active may be in particulate form. The concentration of antiperspirant active in the composition should be sufficient to provide the desired perspiration wetness and odor control from the antiperspirant stick formulation selected. The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

There may be some antiperspirants and/or deodorant embodiments that are substantially free of or completely free of aluminum.

Other Optional Ingredients

The stick compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance.

Non limiting examples of materials can include active components such as bacteriostats and fungiostats, and "non-active" components such as colorants, perfumes, perfume delivery composition, such as cyclodextrins, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

C. Aerosols

Aerosol product of the current invention can include both antiperspirant sprays and deodorant body sprays. Both forms may contain a propellant and a concentrate. The product concentrate may contain, for example a carrier liquid, an antiperspirant or deodorant active, and a perfume.

Propellant

The aerosol compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 90%, 85% 80% 70%, 65%, 60%, 54%, 52%, 50%, 48%, 46%, 44%, or 42%, or any combination thereof, by weight of the total fill of materials stored within the container.

Carrier

A carrier liquid suitable for use in a deodorant body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol. Often ethanol is the predominate carrier liquid in a deodorant body spray.

Carrier liquids suitable for antiperspirant concentrates can include an oil or a mixture of two or more oils. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

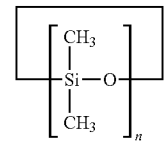

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above).

Antiperspirant or Deodorant Actives

Any of the antiperspirant or deodorant actives listed above herein can be incorporated in the aerosol compositions of the present invention. Aerosol antiperspirant typically include aluminum chlorohydrate, aluminum sesquichlorohydrate, and aluminum dichlorohydrate. Often particulate versions of there actives are used with average particle size ranges from 10-50 microns. Aerosol deodorant body sprays often include bacteriocides or fungicides that are ethanol soluble, these include but are not limited to zinc phenolsulfate and farnesol.

III. Methods of Use

One embodiment of the present invention is a method of removing hair from an underarm comprising the following steps:

a. applying an antiperspirant or deodorant composition to the underarm;
b. at least 6 hours later, wetting the antiperspirant or deodorant composition on the underarm with water; and
c. shaving the underarm with a razor;
wherein said antiperspirant or deodorant composition comprises a component selected from the group consisting of an antiperspirant active, a deodorant active, an odor masking fragrance, and combinations thereof; and
wherein the composition comprises from about 3% to about 20%, by weight of the composition, of a blend of a nonvolatile, low viscosity silicone emollient and a high molecular weight silicone polymer.

In some embodiments, the wetting and/or shaving steps may occur 10 hours after the application of the composition, or 15 hours, 20 hours, or 24 hours after the application of the composition. In some embodiments, the wetting step is not needed, and the user simply applies the composition to the underarm and shaves, either immediately, or 4, 6, 10, 15, 20, or 24 hours later. In some embodiments, the method may further comprise the step of washing the underarm and reapplying the antiperspirant or deodorant composition after the shaving step.

The deodorant and antiperspirant products and compositions of the present invention may be topically applied to the axilla or other area of the skin in any known or otherwise effective method for controlling malodor associated with perspiration. These methods comprise applying to the axilla or other area of the human skin a safe and effective amount of the deodorant or antiperspirant composition of the present invention. "Safe and effective amount" means an amount of the deodorant or antiperspirant composition topically applied to the skin which is effective in inhibiting or minimizing or masking perspiration malodor and/or perspiration at the site while providing increased lubricity during the shave, while also being safe for human use at a reasonable risk/benefit ratio. Thus, a safe and effective amount, as used in the present invention, may, for example, range from about 0.1 gram per axilla to about 2.0 gram per axilla. The compositions are preferably applied to the axilla or other area of the skin one or more times daily, preferably once daily.

It is also contemplated that additional shave preparations may be used in conjunction with this composition to further enhance the shave experience. Shave preparations may be done before shaving and are used to add an additional layer of benefits to the shave experience. Shave preparations used in conjunction with the present invention may contain additional lubricants, soaps, surfactants, oils, and/or anti-irritation agents, including aloe vera, glycerin, panthenol, and combinations thereof.

Razors are also contemplated for use with this invention. Razors having three or more blades typically have the best performance with this invention, as it is believed the thinner design of the blades provides for reduced irritation.

IV. Examples and Test Procedures

The following examples and test procedures detail exemplary compositions of the present invention. These examples are not exhaustive; rather, they are illustrative of the possible formulations of the present invention.

| A. Invisible Solid Formulation | | | |
|---|---|---|---|
| Component | CAS # | Purpose | % w/w |
| ALUMINUM ZIRCONIUM TRICHLOROHYDREX GLY (19% ANHYDROUS) | 134375-99-8 | Antiperspirant active | 14.00 |
| CYCLOPENTASILOXANE | 541-02-6 | Volatile emollient | 31.60 |
| STEARYL ALCOHOL | 112-92-5 | Structurant | 14.00 |
| C12-15 ALKYL BENZOATE | 68411-27-8 | Nonvolatile emollient | 9.50 |
| PPG-14 BUTYL ETHER | 9003-13-8 | Nonvolatile emollient | 6.50 |
| HYDROGENATED CASTOR OIL | 8001-78-3 | Structurant | 3.85 |
| PETROLATUM | 8009-03-8 | Nonvolatile emollient | 3.00 |
| TALC | 14807-96-6 | | 2.10 |
| PHENYL TRIMETHICONE | 73559-47-4 | Nonvolatile emollient | 3.00 |
| MINERAL OIL | 8042-47-5 | Nonvolatile emollient | 1.00 |
| BEHENYL ALCOHOL | 661-19-8 | Structurant | 0.20 |
| DIMETHICONE AND DIMETHICONOL (12%) - DC1503 | | Skin Friction Reducer | 10.00 |
| Fragrance | N/A | | 1.25 |
| | | Total | 100.00 |

| B. Soft Solid Formulation | | | |
|---|---|---|---|
| Component | CAS # | Purpose | % W/W |
| CYCLOPENTASILOXANE | 541-02-6 | Volatile Emollient | 51.75 |
| ALUMINUM ZIRCONIUM TRICHLOROHYDRATE GLY POWDER | 134375-99-8 | Antiperspirant Active | 25.25 |
| FULLY HYDROGENATED HIGH ERUCIC RAPESEED OIL | 129828-27-9 | Structurant | 5.00 |
| DIMETHICONE | 63148-62-9 | Nonvolatile emollient | 5.00 |
| PETROLATUM | 8009-03-8 | Nonvolatile emollient | 3.00 |
| C18-36 ACID TRIGLYCERIDE | 91052-08-3 | Structurant | 1.25 |
| BETA CYCLODEXTRIN WITH FRAGRANCE | MIXTURE | Fragrance delivery system | 3.00 |
| FRAGRANCE | N/A | | 0.75 |
| DIMETHICONE AND DIMETHICONOL (12%) - DC1503 | | Skin Friction Reducer | 5 |
| | | Total | 100.00 |

C. Spray Formulation

| Component | CAS # | Purpose | % W/W |
|---|---|---|---|
| BUTANE, PROPANE, ISOBUTANE | 74-98-6, 75-28-5 | Propellant | 80.20 |
| CYCLOPENTASILOXANE | 541-02-6 | Volatile Emollient | 10.5 |
| ALUMINUM CHLOROHYDRATE | 12042-91-0 | Antiperspirant Active | 5.00 |
| DISTEARDIMONIUM HECTORITE | 94891-31-3 | Structurant | 0.60 |
| DIMETHICONE, 10CST | 63148-62-9 | Nonvolatile emollient | 0.50 |
| TRIETHYL CITRATE | 77-9-0 | Nonvolatile emollient | 0.20 |
| DIMETHICONE AND DIMETHICONOL (12%) - DC1503 | | Skin Friction Reducer | 2 |
| FRAGRANCE | N/A | | 1.00 |
| | | Total | 100.00 |

D. Roll-on Formulation

| Component | CAS # | Purpose | % W/W |
|---|---|---|---|
| ALUMINUM CHLOROHYDRATE | 1327-41-9 | Antiperspirant Active | 14.40 |
| WATER | 7732-18-5 | solvent | 75.95 |
| PPG-15 STEARYL ETHER | 25231-21-4 | Nonvolatile emollient | 3.00 |
| STEARETH-2 | 16057-43-5 | Emulsifier | 1.90 |
| STEARETH-20 | 9005-00-9 | Emulsifier | 1.10 |
| BHT | 128-37-0 | Antioxidant | 0.05 |
| DISODIUM EDTA | 139-33-3 | Chelant | 0.10 |
| DIMETHICONE AND DIMETHICONOL (12%) -DC1503 | | Skin Friction Reducer | 3.00 |
| PERFUME | N/A | | 0.50 |
| | | | 100.00 |

D. Gel Formulation

| Component | CAS # | Purpose | % W/W |
|---|---|---|---|
| ALUMINUM ZIRCONIUM OCTACHLOROHYDREX GLY (29% ANHYDROUS) | 90604-80-1 | Antiperspirant Active | 55.15 |
| WATER | 7732-18-5 | Solvent | 10.95 |
| ALCOHOL DENAT. | 64-17-5 | Solvent | 11.00 |
| PROPYLENE GLYCOL | 57-55-6 | Volatile Emollient | 6.15 |
| PEG/PPG-18/18 DIMETHICONE DC 5225C | 68937-55-3 | Emulsifier | 7.50 |
| DIMETHICONE AND DIMETHICONOL (12%) -DC1503 | | Skin Friction Reducer | 5.00 |
| CYCLOPENTASILOXANE | 541-02-6 | Volatile Emollient | 15 3.5 |
| FRAGRANCE | N/A | | 0.75 |
| | | Total | 100.00 |

Test Method:

Testing Procedure for Determining Coefficient of Friction for Formulations

The following test procedures are utilized to determine the coefficient of friction for formulations on the surface of the skin and illustrate the benefit of the inclusion of a blend of a nonvolatile, low viscosity silicone emollient and high molecular weight silicone polymer in an antiperspirant or deodorant composition. Testing was performed using skin substrates described in U.S. Pat. Nos. 7,954,392 B2 and 8,417,474 B2.

Procedure

Equipment:
KES-SE Surface Tester instrument parameters: (Kato Tech Co., LTD.)
1. Speed; 1.0 mm/sec.
2. Static weight; 50 grams.
3. Sensitivity; H.
4. Probe; aluminum custom probe. Used as is. (Materials 4).
5. KES Software at time of method documentation is Version 7.08E.

Test Procedures:
1. Cut a 9×4 cm piece of polyurethane (PU) substrate material. Lay on a flat and level surface with the textured side up.
2. Obtain a homogenous sample and using a spatula, apply 220±10 mg of sample material to the surface (textured side) of the PU. Spread the material evenly over the entire piece of PU substrate with finger. A nitrile or other non-reactive glove can be used to prevent sample contamination. It is recommended that samples be prepared in duplicate. A control sample(s) and blank substrate runs are also recommended.
3. Immediately after applying the sample material to the PU substrate, place the substrate upon the KES Friction tester platform. Double sided tape is used to affix the substrate to the platform.
   a. Alternatively, the PU substrate with sample applied may be allowed to sit or season for a period of time. This will be dictated by objectives of the test.
4. Obtain the MUI and MMD measurements with the KES friction instrument.
5. Multiple strokes may be performed over the same area or the substrate may be moved to provide a fresh product surface to test. The probe may be cleaned after each test or after several tests. Repeat probe strokes and cleaning frequency of the probe is dictated by the test. Cleaning of the probe is accomplished by carefully wiping the material from the probe with a clean tissue or paper towel and then wiping the probe with an alcohol saturated wipe.

Materials:
1. Polyurethane Skin mimic (see below for preparation).
2. Double Sided Tape. Scotch 3M, Removable Double Stick Tape, ⅜ inch wide. Catalog #109.
3. Bausch & Lomb Sight Saver, Pre-moistened Lens Cleaning Tissue; or equivalent.
4. Aluminum probe, custom made. See drawing (See FIGS. 1-4).

FIGS. 1-4 show the custom-made aluminum probe to be used in the coefficient of friction test method. KES friction Probe. Material: 6061 Aluminum. All measurements inches.

Process for making Skin Surrogate Substrates:

| Materials | Suggested Type (or equivalent) |
|---|---|
| Skin textured metal plate | Purchase from Akron Metal |
| SC-89 Flex Paint Gloss (SFPG1GL) | Burman Industries, Van Nuys CA (818 782 9833) |
| SC-89 Thinner | Burman Industries, Van Nuys CA (818 782 9833) |
| 1 L glass jar, wide mouth | General lab supply |
| 300 ml beaker | General lab supply |

-continued

| Process for making Skin Surrogate Substrates: | |
|---|---|
| Materials | Suggested Type (or equivalent) |
| Paper towels | General lab supply |
| Rubber gloves | General lab supply |
| Pipets | General lab supply |
| Double sided foam tape | 3M # 4046 (1″ × 1/16″) |

Notes:
1. All work must be done in a hood.
2. Use gloves when handling SC-89 thinner/Flex Paint Gloss Procedure:
Polymer Stock Solution Preparation—Use Gloves when Handling SC-89 Thinner/Flex Paint Gloss
1. In a 1 L glass jar (wide mouth) combine 300 g SC-89 Flex Paint Gloss and 300 g SC-89 thinner.
2. Place lid on the jar and shake well to thoroughly mix the gloss paint and thinner.
3. Let the mixture set for 1-2 hours (preferably overnight) to allow air bubbles to dissipate. (Could use vacuum to degas and use immediately).

Plate/Mold Preparation
1. Make sure plate molds are level. Adjust if necessary.

Substrate Making Procedure
1. Pour 250 ml (175 g) of the SC-89 Paint/Thinner mixture into a 300 ml beaker.
2. Begin adding the SC-89 Paint/Thinner to the metal plate slowly (make sure plate is level). Start by pouring along the perimeter and continue in a circular path working toward the center until plate is covered.
3. Let the solvent evaporate for 2 hours.
4. Rotate plate 1800 and re-level if necessary.
5. Pour 250 ml of the SC-89 Paint/Thinner mixture into a 300 ml beaker.
6. Begin adding the SC-89 Paint/Thinner to the metal plate slowly. Start by pouring along the perimeter and continue in a circular path working toward the center until plate is covered.
7. Let dry overnight.
8. Next day, mark top of substrate with marking pen and starting from the edge begin peeling the polymer from the plate.

Figure 5:
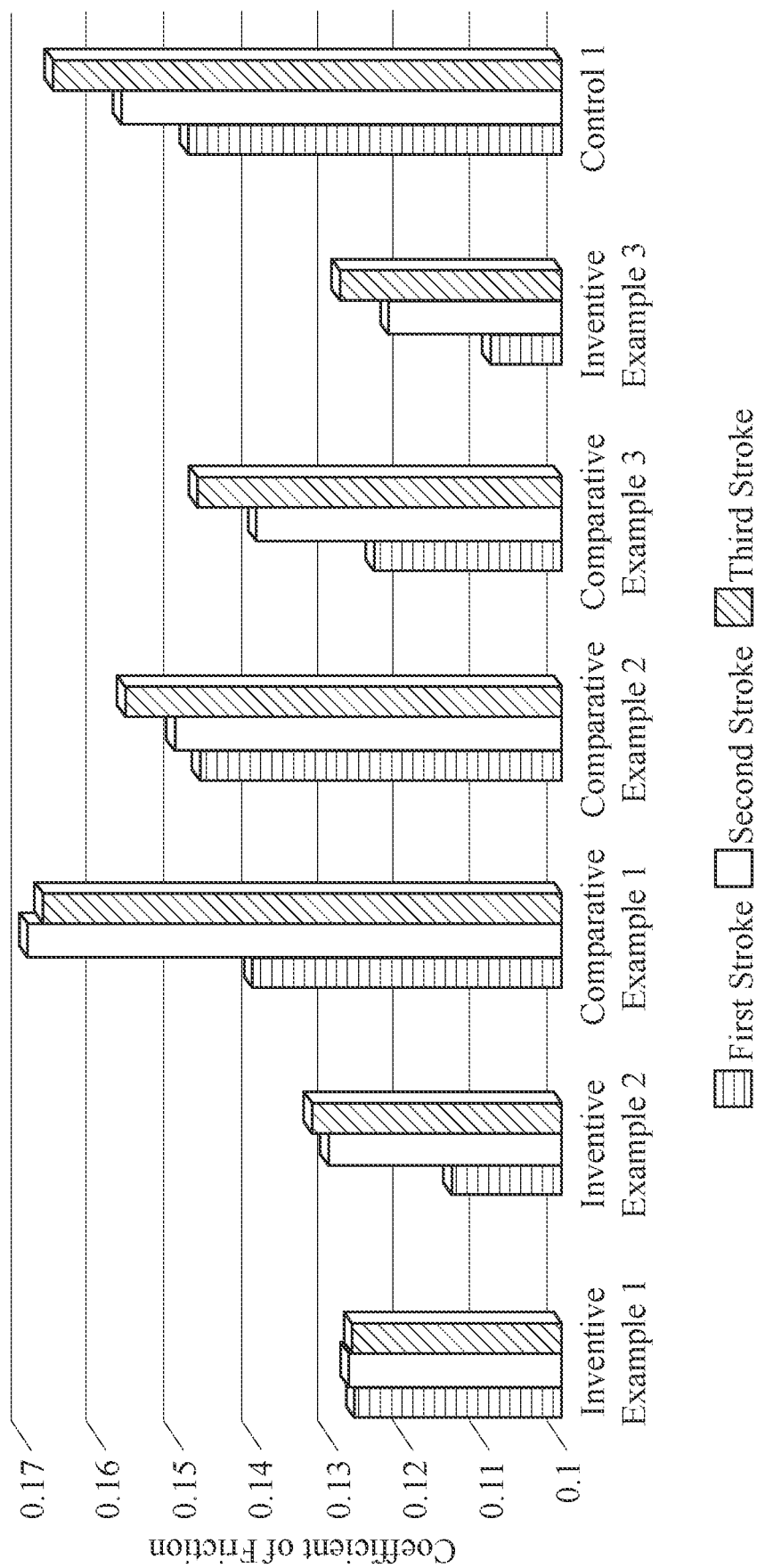
FIG. 5 is a graph of the coefficient of friction for three strokes of a razor for various inventive and comparative examples.

Coefficient of Friction from Soft Solid Formulations of Substantive Friction Reducers The Soft Solid Formulation of Example B above was made with 10%, by weight of the composition, of DC1503, which is a blend of an ultra high viscosity dimethiconol (12%) in a low viscosity dimethicone fluid (88%), resulting in Inventive Example 1. The soft solid formulation Example B was then made with various blends of materials substituted for the DC 1503, resulting in Inventive Example 2 and Inventive Example 3, along with Comparative Examples 1, 2, and 3, as shown below. Using the test method described above, all three Inventive Examples and all three Comparative Examples, along with a control, a soft solid chassis with no blend, were tested to determine the coefficient of friction for three strokes of a razor. Specifically, the control was the soft solid formulation Example B minus the DC1503 blend, with 5% extra cyclopentasiloxane to fill in the missing weight percent of the blend. The results of this testing are illustrated below in Table 1 and the graph in FIG. 5.

TABLE 1

| Example | Inventive Blend of a nonvolatile low viscosity silicone emollient and high molecular weight silicone polymer such as dimethicone or dimethiconol; or Comparative Materials | Trade Name | Conc. in Soft Solid (% w/w) | Coefficient of Friction | | |
|---|---|---|---|---|---|---|
| | | | | First Stroke | Second Stroke | Third Stroke |
| Inventive Example 1 | Dimethicone and Dimethiconol (12%) | DC1503 | 10.00 | 0.1273 | 0.1280 | 0.1272 |
| Inventive Example 2 | Dimethicone (14% High viscosity) | DC1413 | 10.00 | 0.1144 | 0.1304 | 0.1327 |
| Comparative Example 1 | Cyclopentasiloxane and Dimethicone (15% high viscosity) | DC1411 | 10.00 | 0.1402 | 0.1696 | 0.1681 |
| Comparative Example 2 | Dimethicone ( High viscosity 600,000 cP) | DC1418 | 10.00 | 0.1474 | 0.1508 | 0.1570 |
| Comparative Example 3 | C13-16 Isoparaffin, Dimethicone (14% High viscosity), C10-13 Isoparaffin | DC 25-320 | 10.00 | 0.1247 | 0.1400 | 0.1476 |
| Inventive Example 3 | Phenyl-Trimethicone, and Dimethiconol (14%) | DC CB-1556 | 10.00 | 0.1095 | 0.1228 | 0.1295 |
| Control 1 | Soft Solid Chassis | N/A | Control | 0.1488 | 0.1573 | 0.1665 |

Inventive Examples 1, 2, and 3 showed a reduced skin friction via the addition of a non-volatile low viscosity silicone emollient and high molecular weight silicone polymer. Inventive Example 1, a blend of 5 cst dimethicone and an ultrahigh molecular weight dimethiconol, maintained the lowest coefficient of friction across all three strokes. Additionally, the composition in Inventive Example 1 had the smallest change in coefficient of friction between the first stroke and the third stroke. Inventive Example 2, a blend of 5 cst dimethicone and an ultrahigh molecular weight dimethicone, showed a reduction in skin friction versus the control, but also a larger difference between the first and third stroke. Inventive Example 3, a blend of phenyl trimethicone and an ultrahigh molecular weight dimethicone, showed similar performance to Inventive Example 2.

Conversely, Comparative Example 1, a blend of volatile cylcopentasiloxane and an ultrahigh molecular weight dimethicone, showed a small reduction for the first stroke, but no benefit versus the control for subsequent strokes. Similarly, Comparative Example 2, a blend of volatile isoparaffins and ultrahigh molecular dimethicone, showed a small reduction for the first stroke, but no benefit versus control for subsequent strokes. Comparative Example 3, a blend of 350 cst dimethicone and an ultrahigh molecular weight dimethicone, showed similar skin friction to the control.

Without being bound by theory, it is believed that this benefit is provided when the high molecular weight silicone polymer is solvated by the low viscosity dimethicone, allowing it to lay flat on the skin surface where it can reduce friction between the razor and the skin surface. If the high molecular weight silicone polymer is not solvated, it can form a random coil on the surface and be unable to provide that benefit. Moderate to high viscosity dimethicones, i.e. 350 cst dimethicone, are not believed to solvate the high molecular weight silicone polymer sufficiently to provide this benefit. Moreover, loss of solvation via evaporation of a volatile emollient, i.e. cyclopentasiloxane or volatile isoparaffins) may allow the high molecular weight silicone polymer to return to a coil state on the skin surface, thereby not providing the desired benefit.

Coefficient of Friction Sensitivity from Soft Solid Formulations

Utilizing the above referenced testing method, the Soft Solid Formulation of Example B was tested, with varying concentrations of the blend. The results of this testing are illustrated below in Table 2. At 10% DC1503 (Inventive Example 1), the benefit, according to this data, appears to be maximized.

TABLE 2

| Trial # | Blend of 5 cst dimethicone and high molecular weight dimethiconol | Coefficient of Friction | | |
|---|---|---|---|---|
| | | Average First Stroke | Average Second Stroke | Average Third Stroke |
| Control 2 | 0% | 0.1405 | 0.1447 | 0.1431 |
| 1 | 5% DC1503 | 0.118 | 0.133 | 0.139 |
| 2 | 7.5% DC1503 | 0.111 | 0.121 | 0.127 |
| 3 | 10% DC1503 | 0.112 | 0.117 | 0.108 |
| 4 | 12.5% DC1503 | 0.093 | 0.106 | 0.109 |
| 5 | 15% DC1503 | 0.100 | 0.100 | 0.100 |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of removing hair from an underarm comprising:
   a. applying a deodorant or antiperspirant composition to the underarm; and
   b. shaving the underarm with a razor;
   wherein said composition comprises:
      one or more of the following components: an antiperspirant active, a deodorant active, and/or an odor masking fragrance;
      from about 30% to about 70% of a volatile emollient comprising a volatile silicone;
      from 3% to about 20%, by weight of the composition, of a blend comprising:
         a dimethicone having a viscosity less than about 100 cps; and
         a dimethiconol having a molecular weight greater than about 100 kilodaltons;
      wherein the composition is free of added water;
      wherein the composition is in a form chosen from a solid stick or a soft solid.

2. The method of claim 1, wherein the blend comprises from about 5% to about 20%, by weight of the blend, of the dimethiconol.

3. The method of claim 1, further comprising a step of wetting the composition on the underarm with water.

4. The method of claim 3, further comprising a step of applying a shave preparation after the wetting step.

5. The method of claim 4, wherein the composition further comprises a perfume delivery composition.

6. The method of claim 5, wherein the perfume delivery composition is activated by the wetting step or the shave preparation step.

7. The method of claim 4, wherein the wetting step and the shave preparation step occur at least six hours after applying the composition.

8. The method of claim 1, wherein the razor comprises at least three blades.

9. The method of claim 1, further comprising the step of washing the underarm and reapplying the composition after the shaving step.

10. The method of claim 1, wherein the composition comprises from about 10% to about 20%, by weight of the composition, of the blend of the dimethicone and dimethiconol.

11. The method of claim 1, wherein the dimethiconol has a molecular weight of at least about 300 kilodaltons.

12. The method of claim 1, wherein step (b) occurs at least 20 hours later.

13. The method of claim 1 wherein the composition is free of anionic surfactant.

14. The method of claim 1 wherein the volatile emollient comprises cyclopentasiloxane.

* * * * *